(12) United States Patent
Kaiser et al.

(10) Patent No.: US 6,695,794 B2
(45) Date of Patent: Feb. 24, 2004

(54) ACTIVE TREMOR CONTROL SYSTEM

(75) Inventors: Kenneth W. Kaiser, North Reading, MA (US); Gary E. Hall, Alexandria, VA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 227 days.

(21) Appl. No.: 10/074,330

(22) Filed: Feb. 12, 2002

(65) Prior Publication Data

US 2003/0006357 A1 Jan. 9, 2003

Related U.S. Application Data

(63) Continuation-in-part of application No. 09/260,685, filed on Mar. 2, 1999, now Pat. No. 6,234,045.
(60) Provisional application No. 60/269,127, filed on Feb. 15, 2001.

(51) Int. Cl.[7] ............................................... A61B 5/103
(52) U.S. Cl. ..................................................... 600/595
(58) Field of Search ........................... 600/595; 601/46, 601/78, 79, 80, 81, 82, 83

(56) References Cited

U.S. PATENT DOCUMENTS

| | | | |
|---|---|---|---|
| 5,058,571 A | | 10/1991 | Hall |
| 5,201,772 A | * | 4/1993 | Maxwell ........................ 623/24 |
| 5,291,975 A | | 3/1994 | Johnson et al. .............. 188/378 |
| 5,553,514 A | | 9/1996 | Walkowc ....................... 74/574 |
| 5,560,589 A | * | 10/1996 | Gran et al. ...................... 267/3 |
| 5,809,843 A | | 9/1998 | Barger et al. .................. 74/574 |
| 6,234,045 B1 | | 5/2001 | Kaiser ........................... 74/574 |
| 6,458,089 B1 | * | 10/2002 | Ziv-Av ........................ 600/595 |

FOREIGN PATENT DOCUMENTS

| | | |
|---|---|---|
| FR | 2706559 A1 | 6/1993 |
| JP | 3-168442 | 7/1991 |

OTHER PUBLICATIONS

Hall, Gary Ellis, Active Tremor Control of Human Motion Disorder, Gary Ellis Hall, Jun., 2001.

* cited by examiner

*Primary Examiner*—Eric F. Winakur
(74) *Attorney, Agent, or Firm*—Iandiorio & Teska

(57) ABSTRACT

A light weight, wearable, and balanced active tremor control system including a mount; a proof mass frame moveable with respect to the mount; at least one actuator on the proof mass frame for imparting a force on the mount; a motion sensor for detecting movement of the mount due to tremors; and a controller for driving the actuator in response to the motion sensor.

27 Claims, 11 Drawing Sheets

ACTIVE TREMOR CONTROL SYSTEM

RELATED APPLICATIONS

This application is a continuation in-part application of application Ser. No. 09/260,685 filed Mar. 2, 1999 (now U.S. Pat. No. 6,234,045) and also claims the benefit of Provisional Application Serial No. 60/269,127 filed Feb. 15, 2001.

FIELD OF THE INVENTION

This invention relates to a lightweight, wearable, and, in some embodiments, balanced active tremor control system which, in one embodiment, features a tremor suppressing wrist cuff.

BACKGROUND OF THE INVENTION

Uncontrollable tremors afflict a significant portion of the population adversely affecting an individual's ability to perform physical tasks such as eating, drinking, reading, and walking.

Moreover, even when tremor causing medical problems are not present, even slight normal tremors can adversely effect an individual's ability to precisely perform certain delicate functions including using surgical instruments and performing technical procedures and operations.

As a result, those skilled in the art have long sought to control tremors. Traditional vibration isolation or suppression systems incorporating actuators and used in connection with vibrating machinery do not work well when used in conjunction with human limbs subject to tremors because there is no fixed in place structure available on which to mount the actuators for the actuator reaction force.

In U.S. Pat. No. 5,058,571, hereby incorporated herein by this reference, a hand-held gyroscope device is shown to be firmly held against the backside of the human hand in an attempt to reduce or eliminate the effect of naturally occurring tremors. Unfortunately, the resulting device hinders all motion instead of just damping tremors.

Passively damping tremors, for example, by using a mass coupled to a wrist by resilient members may control tremors but would have to be specifically tuned to meet each individual's needs and also presents certain other disadvantages.

Any wearable, active vibration control device, besides being effective at controlling tremors, must be lightweight and preferably balanced and not interfere with an individual's intended movements.

SUMMARY OF THE INVENTION: I

It is therefore an object of this invention to provide a lightweight tremor control system.

It is a further object of this invention to provide a wearable active tremor control system.

It is a further object of this invention to provide such an active tremor control system which can be balanced.

It is a further object of this invention to provide a tremor suppressing wrist cuff.

It is a further object of this invention to provide an active tremor control system which is more effective at controlling tremors.

It is a further object of this invention to provide such a system which can be worn on the wrist, the forearm, the hand, or the leg.

It is a further object of this invention to provide such a system which can be used by people with medical problems which cause tremors.

It is a further object of this invention to provide such a system which can be used by people with no tremor causing medical problems but who need to manipulate instruments or devices more accurately.

It is a further object of this invention to provide such a system which can be attached directly to an instrument or device.

The invention results from the realization that a wearable device for actively controlling tremors using a proof mass stabilizer can only be connected to the wearer's body part (e.g., the wrist) and, that being the case, there is no fixed structure on which to mount the actuators but, by employing a wearable proof mass frame housing the actuators which then act on the mounting structure, the actuators themselves become proof masses for the system resulting in a lightweight, wearable, and balanced tremor control system.

This invention features a lightweight, wearable, and balanced active tremor control system comprising a mount; a proof mass frame moveable with respect to the mount; at least one actuator on the proof mass frame for imparting a force on the mount; a motion sensor for detecting displacement of the mount; and a controller for driving the actuator in response to the motion sensor. In the preferred embodiment, there are two voice coil linear actuators orthogonally oriented on the proof mass frame and two accelerometers orthogonally oriented on the mount.

The preferred proof mass frame includes a central section interconnected with the mount and a pair of arms depending therefrom and a weight attached to the end of each arm. The central section of the frame includes two angled actuator housings and the mount is unitary in construction and spans the central section of the proof mass frame. In the preferred embodiment, the mount includes two planar side surfaces and a top planar surface. Two ball slide mechanisms interconnect the proof mass frame and the mount. The housing portion of each ball slide mechanism is fixed with respect to the mount and the sliding arm portion of each ball slide mechanism is physically connected to an actuator.

Typically, the accelerometers are mounted with respect to the mount such that the input axis is parallel to the force axis of the actuators. Further included may be means for fixing the position of the proof mass with respect to the mount and for sensing the position of the proof mass frame with respect to the mount, e.g., two linear voltage displacement transducers, one portion of each attached to the mount, the other portion of each attached to the proof mass frame.

The tremor suppression wrist cuff of this invention features a wrist mount including a top surface and angled surfaces disposed over the ulna and radius bones of the human wrist, respectively; a proof mass frame moveable with respect to the wrist mount; and a pair of actuators each connected to the proof mass frame and an angled surface of the wrist mount to apply force to the angled surfaces of the wrist mount and to the ulna and radius bones of the wrist. Typically, the proof mass frame includes angled actuator housings and each actuator has a magnet disposed in an actuator housing. A pair of ball slide mechanisms each include an arm slidable in a housing to allow the actuators to move laterally. Each actuator has a coil mounted to an arm and the housing of each ball slide mechanism is mounted to an angled surface of the wrist mount. Also included may be a pair of guide pins slidably disposed through the proof mass frame and each connected on one end to an adapter plate which secures the coil of each actuator to its respective arm of the ball slide mechanism to guide the actuators. A pair of transformers each including a core may be mounted to the top surface of the wrist mount with the moveable part mounted to an adapter plate for sensing and adjusting the position of the proof mass frame relative to the wrist mount. Typically, the proof mass frame includes a pair of arms depending therefrom and there is a weight attached to each arm so that the center of mass of the wrist cuff is at the center of the wrist.

The active tremor control system of this invention features a mount attachable to a device or a body part; a proof mass frame moveably joined with respect to the mount; at least one sensor for detecting vibrations of the mount; and at least one actuator disposed to apply a force to the proof mass frame with respect to the mount to thereby suppress vibrations of the mount. In the preferred embodiment, there are two independently driven actuators for adjusting the position of the proof mass frame with respect to the mount.

In the preferred embodiment there are two sensors, one accelerometer and one linear voltage displacement transducer (LVDT). The LVDT provides a signal to the controller that commands the actuator to keep it nominally centered in the range of actuation. The purpose of this is to counteract the force of gravity. The accelerometer provides a signal to the controller that commands the actuator to quell the tremors.

BRIEF DESCRIPTION OF THE DRAWINGS

Other objects, features and advantages will occur to those skilled in the art from the following description of a preferred embodiment and the accompanying drawings, in which.

DISCLOSURE OF THE PREFERRED EMBODIMENT

Figure 1:
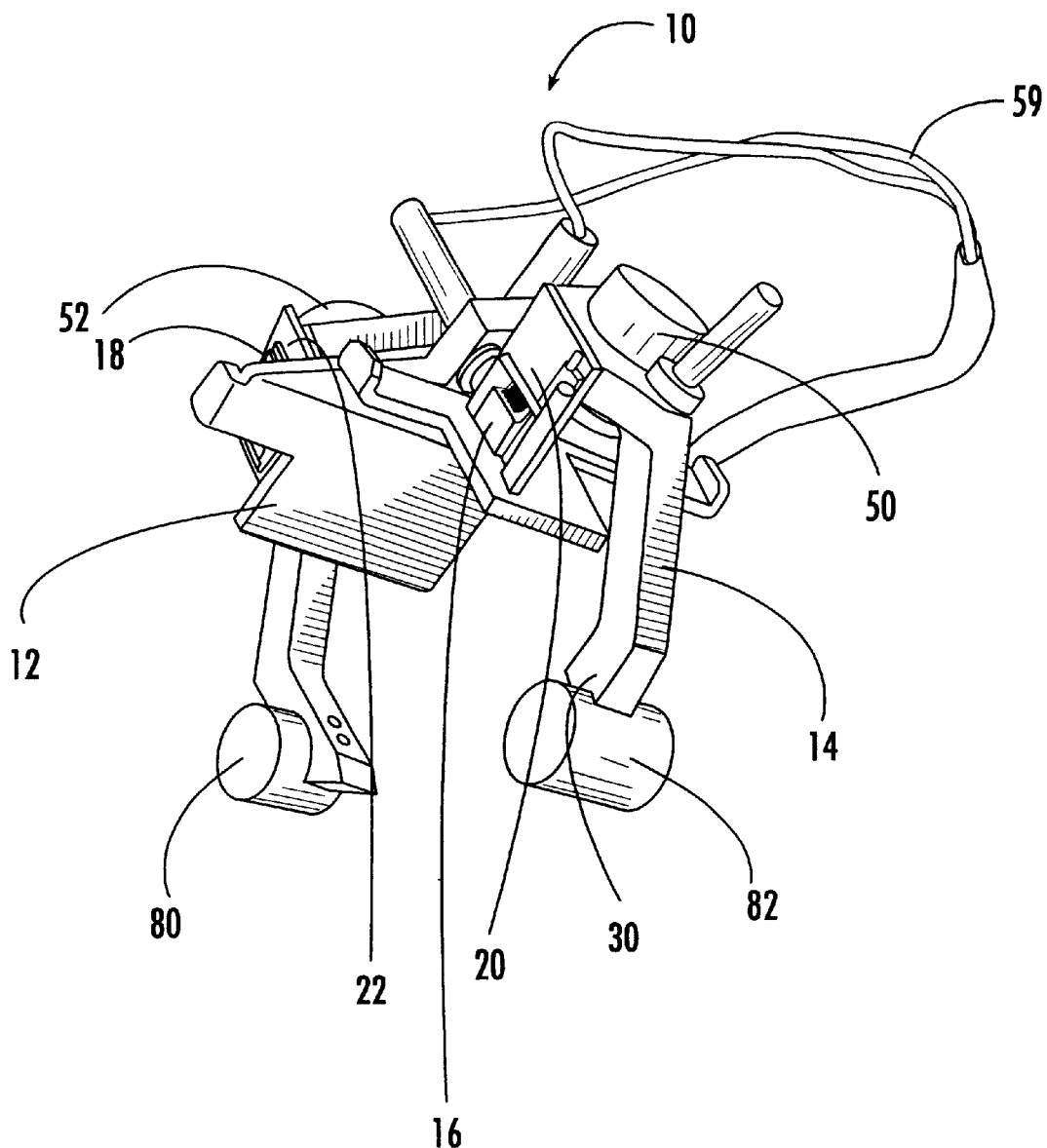
FIG. 1 is a schematic three-dimensional view of one embodiment of the active tremor control system of the subject invention.
Figure 2:
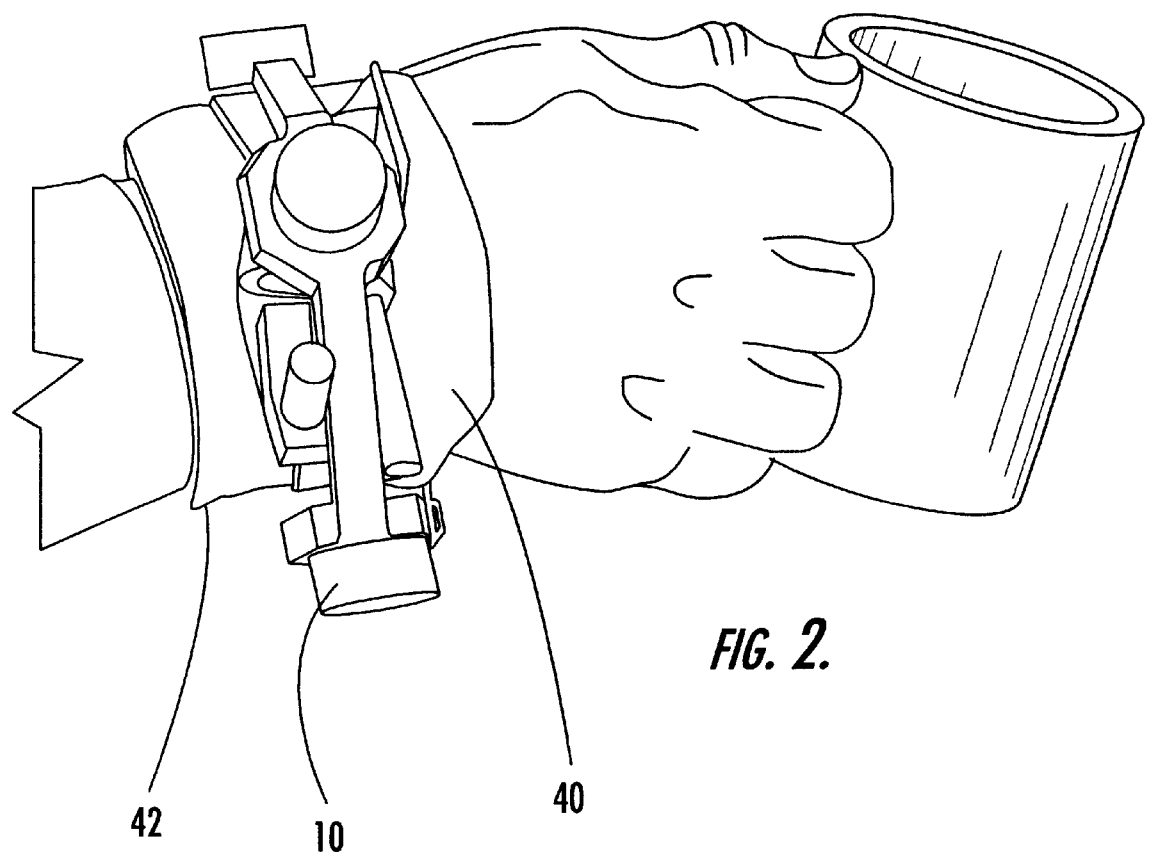
FIG. 2 is a schematic view showing how the active tremor control system shown in FIG. 1 is strapped to a user's wrist in order to assist the wearer in performing daily activities such as drinking from a coffee mug.
Figure 3:
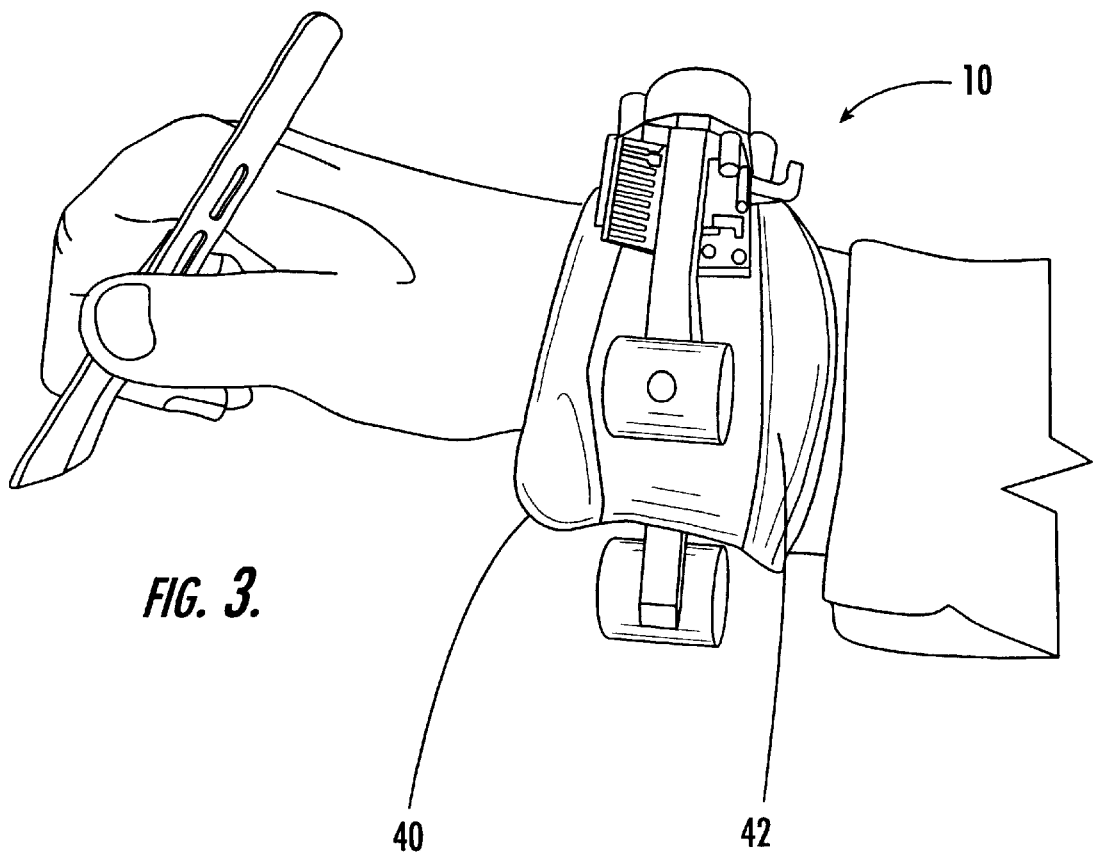
FIG. 3 is a schematic view of the active tremor control system shown in FIG. 1 strapped to a user's wrist in order to assist in the use of a precise instrument such as a scalpel.

Tremor control system 10, FIG. 1, in the preferred embodiment, includes mount 12, proof mass frame 14 moveable with respect to mount 12, and accelerometers 16 and 18 on circuit boards 20 and 22 mounted to mount 12 via standoffs as shown for standoff 30. Mount 12 is strapped to the user's wrist, for example, by Velcro straps 40 and 42, FIGS. 2–3. Accelerometers 16 and 18 then sense tremors of the user's hand and wrist area and output a corresponding voltage representing the movement of the user's wrist and also the direction of movement.

In response to this movement, actuators 50 and 52 mounted on frame 14 impart corresponding off-setting forces on mount 12 to quell the tremors. A controller (not shown in FIG. 1) located either on-board circuit boards 20 and/or 22 or connected thereto by wiring harness 59 and located, for example, on the user's belt, monitors the voltage levels output by accelerometers 16 and 18 and, in response, drives actuators 50 and 52 to impart forces which cancel the movements detected by accelerometers 16 and 18 in a continuous, closed loop fashion.

In this way, people with uncontrollable tremors can more easily perform such routine tasks as drinking coffee (FIG. 2) and better perform other daily tasks and, in addition, surgeons and technicians and other skilled laborers can better perform delicate and precise tasks (see FIG. 3) even when they do not have a medical condition which causes tremors.

As shown in the FIG. 1, actuators 50 and 52 are orthogonally oriented on proof mass frame 14. This arrangement is accomplished by mounting lightweight (3.2 ounce) voice coil linear actuators (available from BEI Sensors and Systems, Corp., Kimco Magnetics Division as Model No. LA10-12-027A) which provides plus or minus 0.180 inches of stroke and three pounds of force in angled housing 60 and 62, FIG. 4 of proof mass frame 14. The magnetized ends of the actuators, referred to as the "field ends", are mounted to proof mass frame 14 since they are the most massive. The electric or coil ends of the actuators are mounted on linear ball slides discussed infra.

Figure 4:
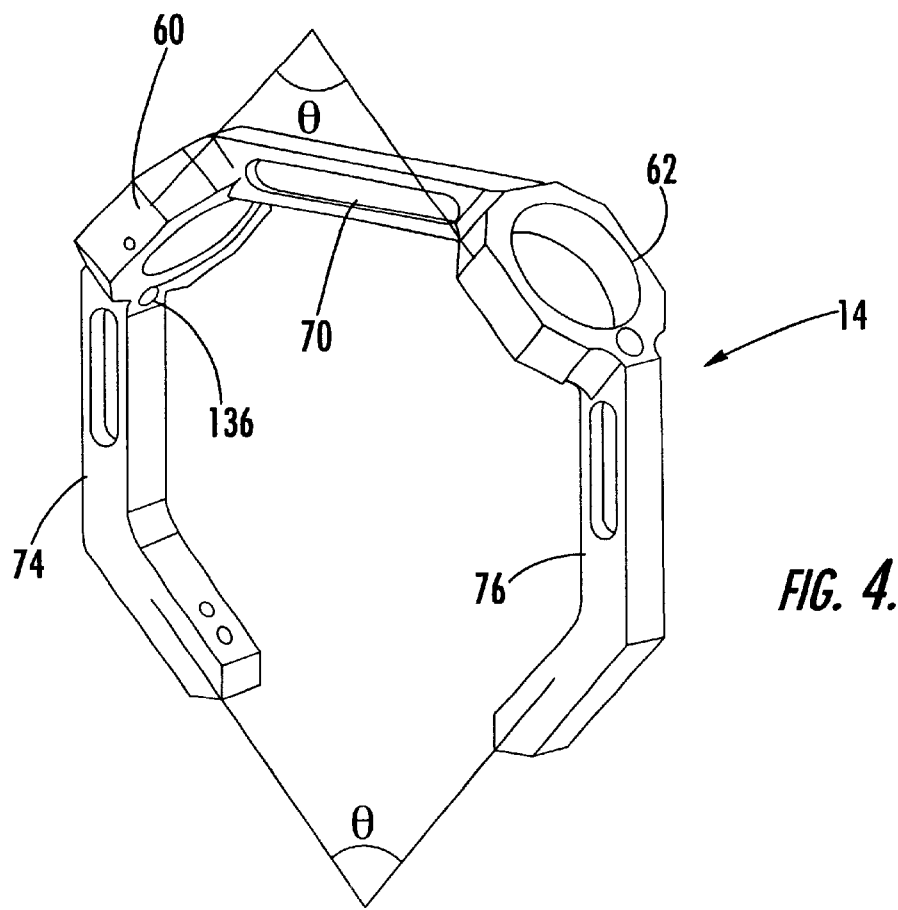
FIG. 4 is a three dimensional view of the proof mass frame portion of the active tremor control system shown in FIG. 1.
Figure 5:
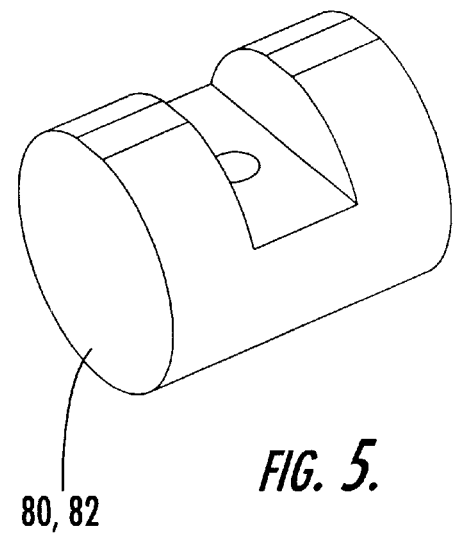
FIG. 5 is a three dimensional view of a weight attached to the end of the arms of the proof mass frame shown in FIGS. 1 and 4 in order to provide balance.
Figure 6:
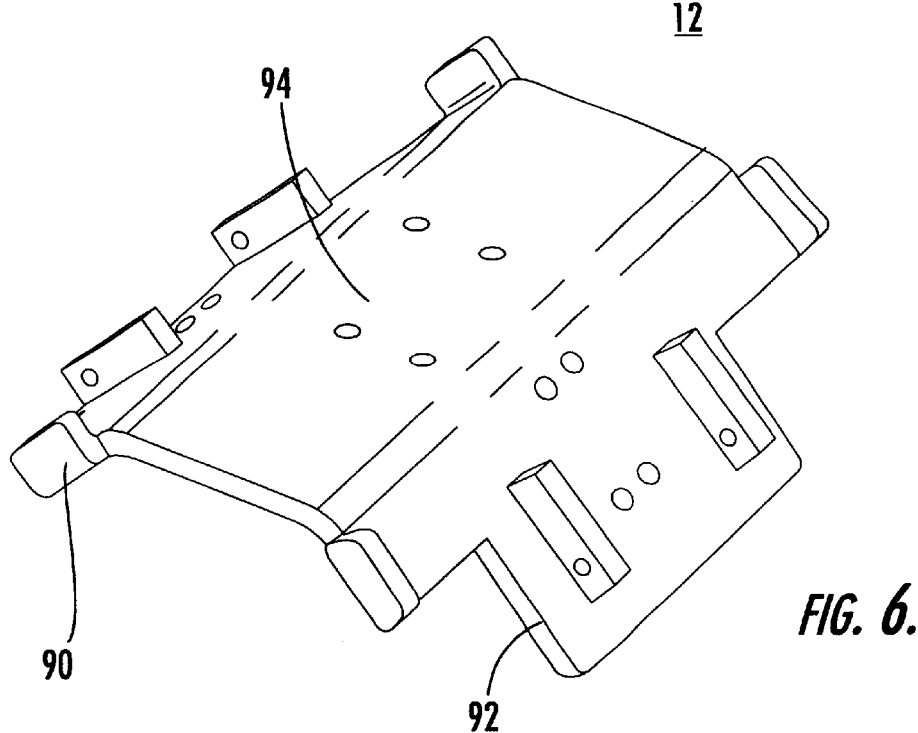
FIG. 6 is a three dimensional view showing the mounting structure for the active tremor control system shown in FIG. 1.
Figure 7:
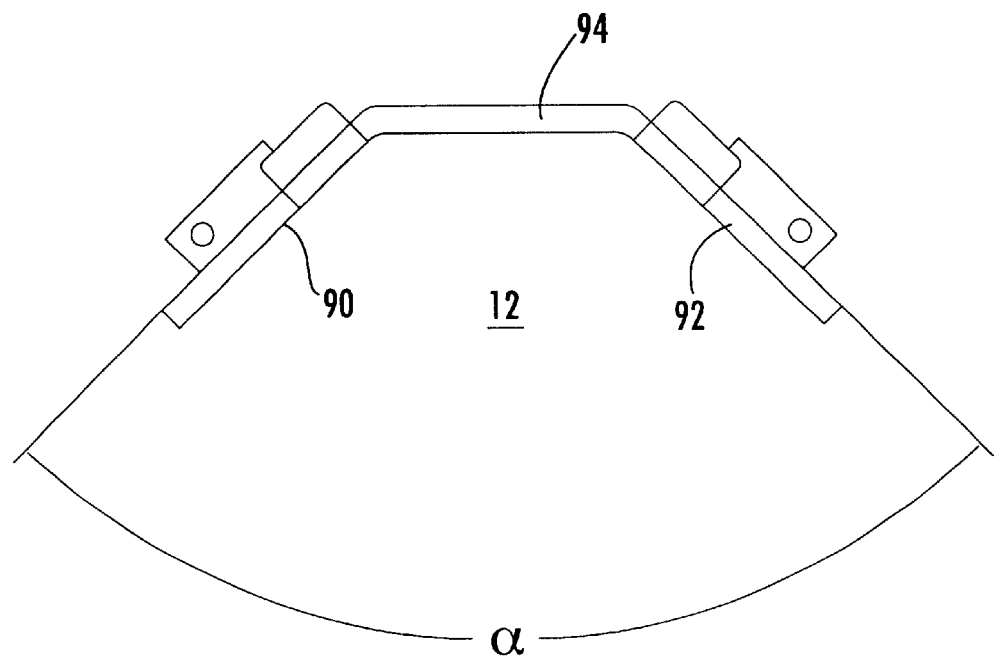
FIG. 7 is an end view of the mounting structure shown in FIG. 6.

As shown in FIG. 4, aluminum proof mass frame 14 includes central section 70 and a pair of arms 74 and 76 depending therefrom. Angle θ is preferably 90°. Two 117.5 gram tungsten weights 80 and 82, FIGS. 1 and 5 are attached to the ends of each arm 74, 76 of proof mass frame 14 to assist in maintaining a center of mass for system 10 at the approximate center of the user's wrist. Mount 12, FIGS. 6–7 is unitary in construction and spans the central section 70 of proof mass frame 14, FIG. 4. Mount 12, FIG. 6 includes two angled planar side surfaces 90, 92, FIG. 7 and top planar surface 94. Angle γ is 90°. A padded material such as foam can be attached to the bottom of mount 12 for added comfort.

Figure 8:
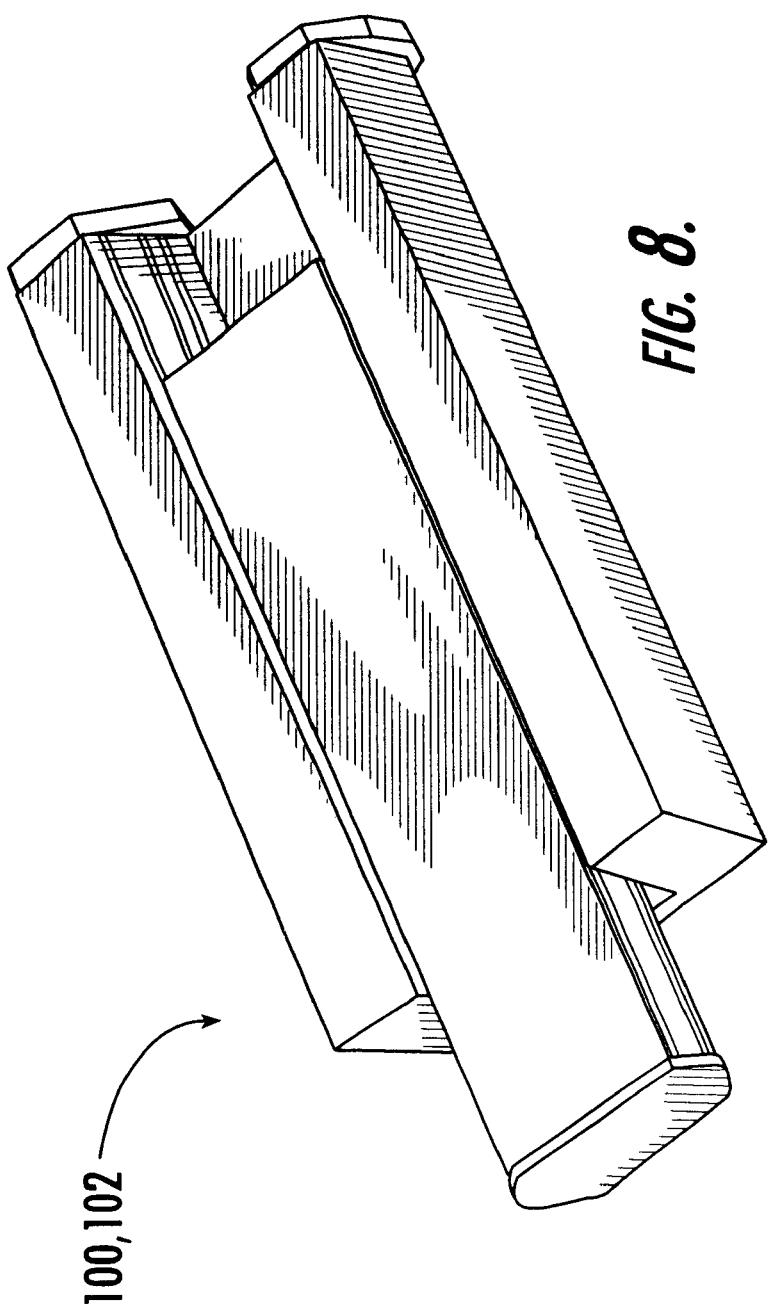
FIG. 8 is a schematic view showing the ball slide mechanisms for the active tremor control system of the subject invention.
Figure 9:
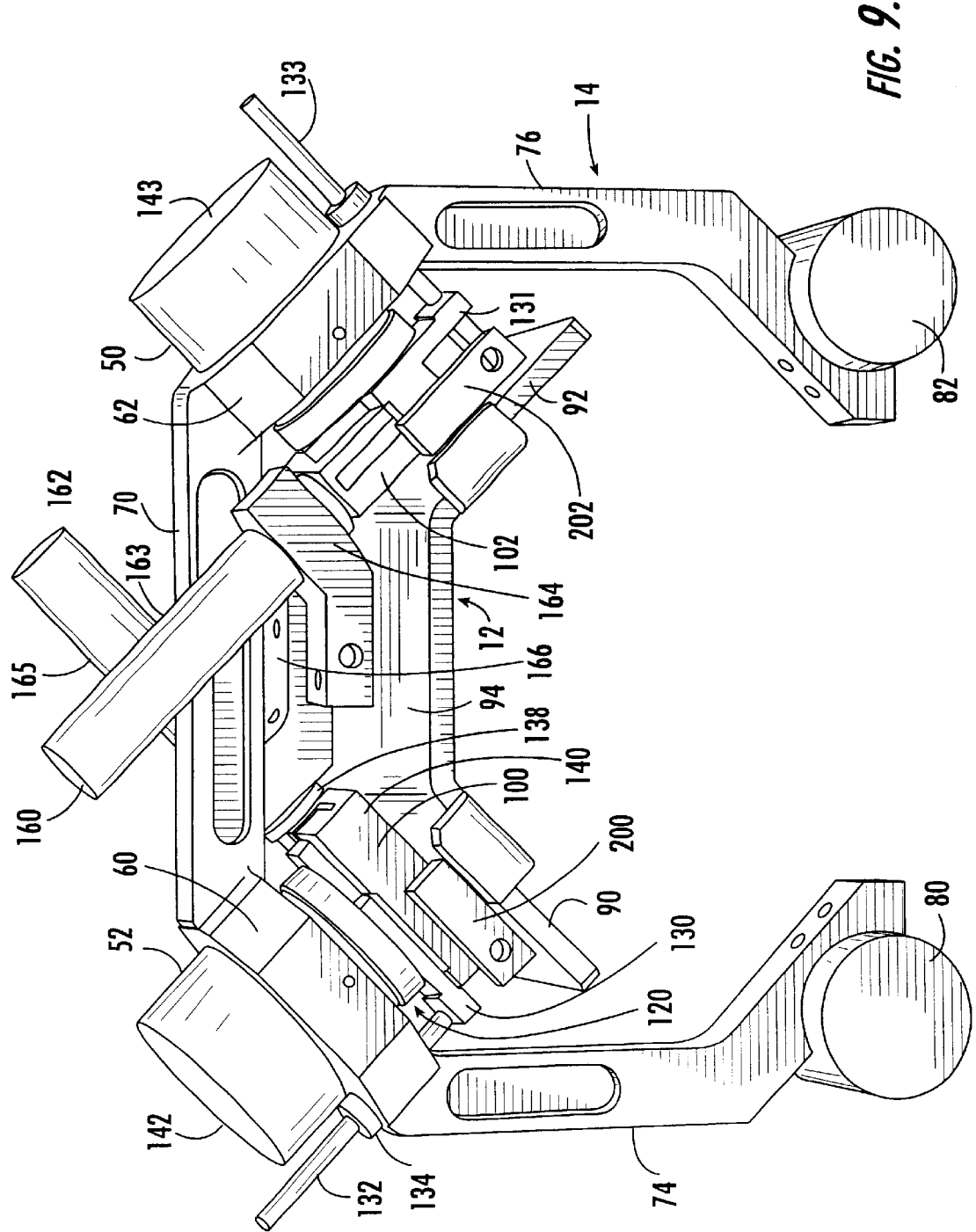
FIG. 9 is a schematic view showing the primary components associated with the tremor suppressing wrist cuff of the subject invention with the actuators and the ball slide mechanisms in their centered positions.
Figure 10:
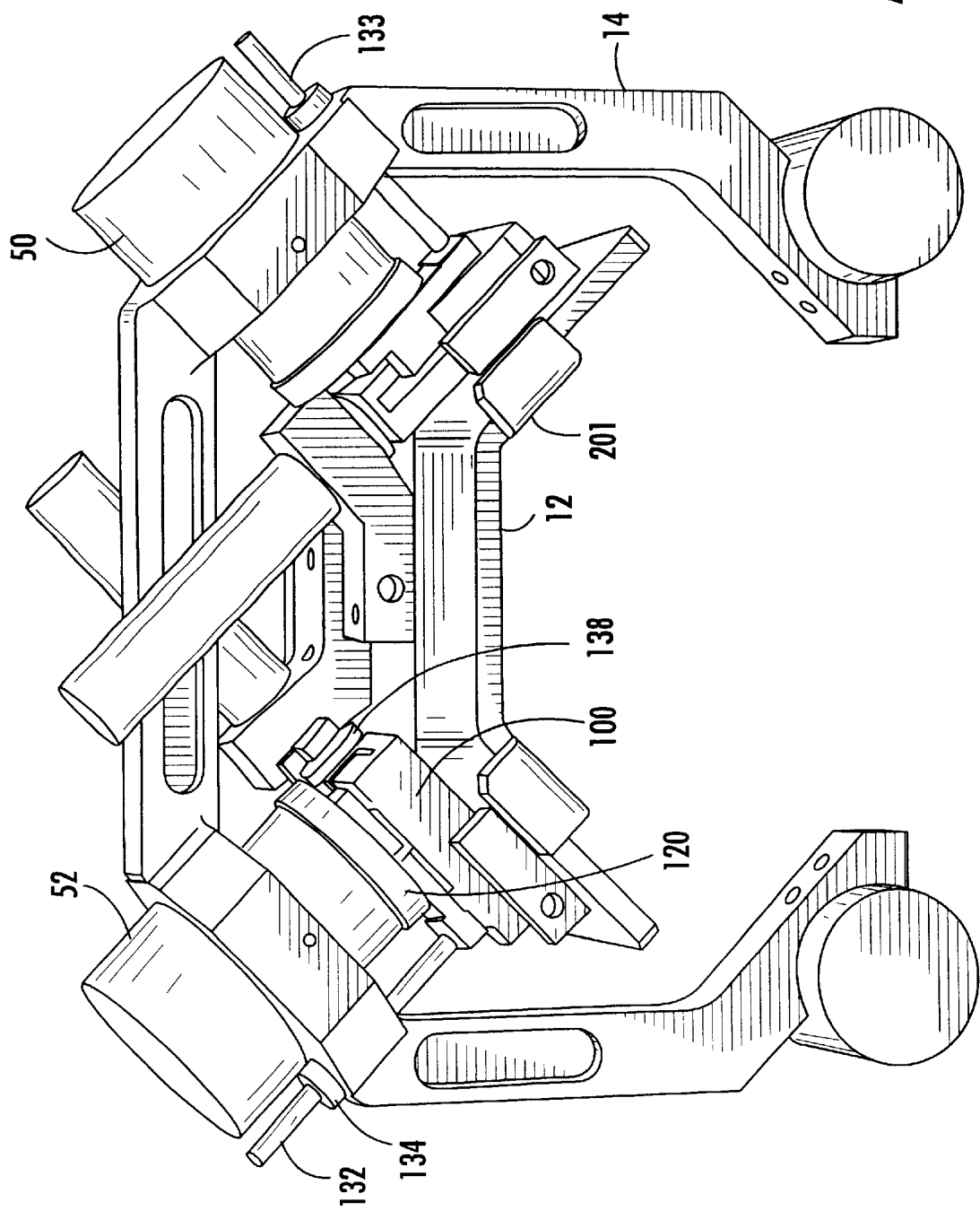
FIG. 10 is a view similar to FIG. 9 except now the actuators are both in their fully extended positions.
Figure 11:
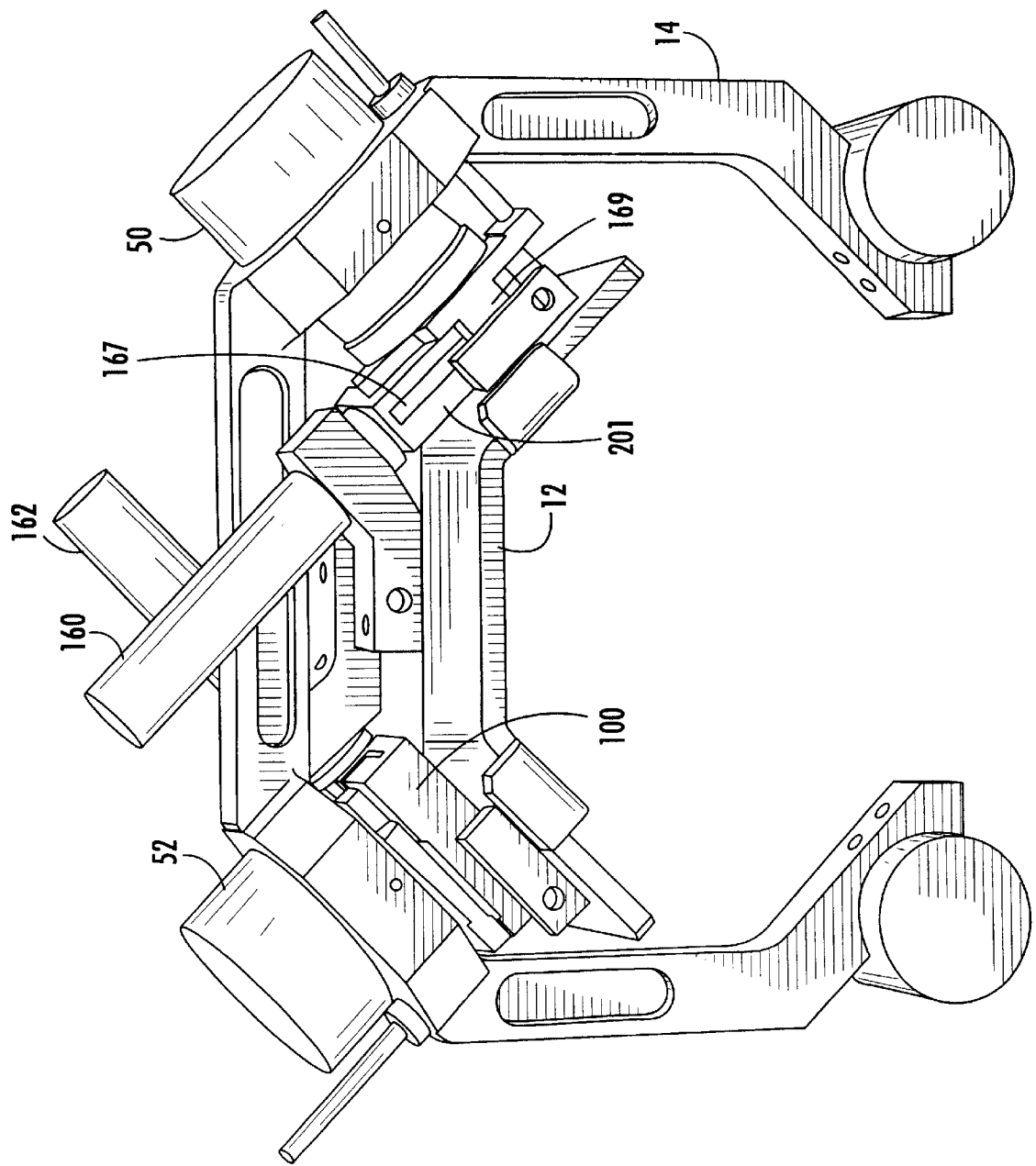
FIG. 11 is also a view similar to FIG. 9 except now one actuator is fully extended and the other actuator is fully contracted.

Ball slides 100, 102, FIG. 8 are preferably used to interconnect the proof mass frame and the mount as shown in FIGS. 9–11.

The actuator coil 120 of actuator 52 is fitted with adapter plate 130 (see also FIG. 13) constrained by guide pin 132 which moves up and down through teflon bushing 134 (see FIG. 14) in orifice 136, FIG. 4 of proof mass frame 14. Adapter plate 130, FIG. 9 is secured to sliding arm 138 of ball slide 100. Housing 140 of ball slide 100 is fixed to angled side 90 of mount 12. Magnet 142 of actuator 52 is mounted in housing 60 of proof mass frame 14 as shown. Actuator 50 is similarly mounted with respect to mount 12.

Linear voltage displacement tranducers (LVDTs) 160 and 162 are secured to mount 12 via mounting brackets 164, 166, respectively (see FIG. 12) and are used to center actuators 52 and 50 against the force of gravity. In FIG. 9, the actuators are centered. In FIG. 10, actuators 50 and 52 are shown to be fully extended. In FIG. 11, actuator 52 is fully contracted but actuator 50 is still fully extended. LVDTs 160 and 162 are thus used as sensors to return the actuators to a central position mitigating the effect of gravity and serve as the means for fixing the position of proof mass frame 14 with respect to mount 12. Thus, if LVDT 162 is activated, the position of actuator 52 will return to the position shown in FIG. 10. The LVDTs also sense the position of proof mass frame 14 with respect to mount 12. The LVDTs provide a signal to the controller. The controller commands the actuators to provide a force to center the actuators against the force of gravity. The actuator provides two forces—one from LVDT to center it—the other from accelerometer to quell the tremor.

FIGS. 9–11 depict one specific embodiment of the tremor control system of this invention, namely a tremor suppressing wrist cuff. Wrist mount 12 includes top surface 94 and angled surfaces 90 and 92 which are disposed over the ulna and radius bones of the human wrist, respectively. Proof mass frame 14 is moveable with respect to wrist mount 12. Actuators 50 and 52 are each connected to proof mass frame 14 and also an angled surface 90, 92 of wrist mount 12 to apply force to the ulna and radius bones of the wrist. As shown, proof mass frame 14 includes angled actuator housings 60 and 62 for housing the magnet portion 142, 143 of actuators 52, 50 respectively. Ball slide mechanisms 100, 102 each include an arm (see arm 138 of ball slide mechanism 100) slidable in housing 140 to thereby allow actuators 52 and 50 and proof mass frame 14 to move laterally with respect to wrist mount 12. Each actuator 50, 52 has a coil 120 as shown for actuator 52 mounted to arm 138 of ball mount slide mechanism 100 which in turn is mounted to angled surface 90 of wrist mount 12.

Figure 13:
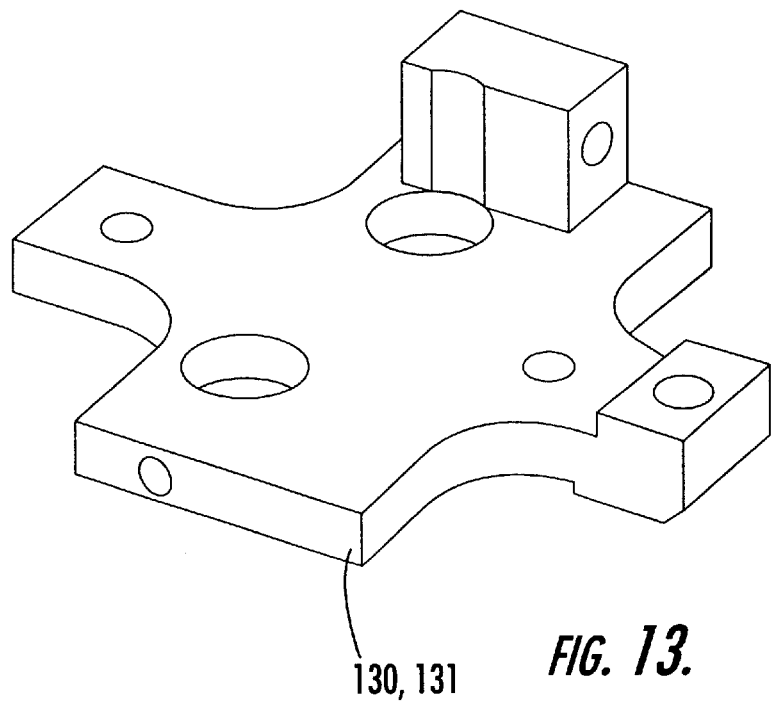
FIG. 13 is a three dimensional view of the adapter plate disposed between the actuator and the ball slide mechanism of the wrist cuff shown in FIG. 9.
Figure 14:
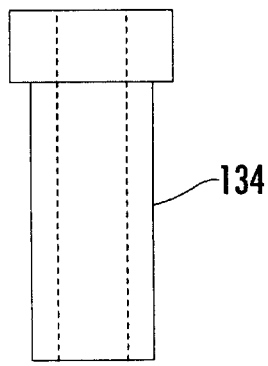
FIG. 14 is a plan view of the teflon bushing associated with the guide pin of the tremor suppressing wrist cuff of this invention.

Guide pin 132 is slidably disposed through proof mass frame 14 via teflon bushing 134, FIG. 14 and connected on its distal end to adapter plate 130, FIG. 13 which secures the coil end 120, FIG. 9 of actuator 52 to arm 138 of ball slide mechanism 100 to guide actuator 52 as it extends and contracts. LVDT sensors 160 and 162 each include core 163 and 165, respectively, mounted to top surface 94 of wrist mount 12 via mounting brackets 164, 166 respectively. The moveable part of the transformers, best shown at 167 in FIG. 11, is connected to the adapter plate ear 169 such that the LVDTs can both sense and adjust the position of proof mass frame 14 relative to wrist mount 12.

In this specific design, wrist mount 12 with the three planar surfaces is able to transmit forces to the ulna and radius bones of the forearm and, as such, the force axis of the actuators is directed right at these wristbones. Del-tron model D-1 linear ball slides 100 and 102 allow the actuators to translate plus or minus 0.25 inches orthogonally to their axis of actuation. The ball slide mechanisms are attached directly to wrist mount 12 in order to keep the profile of the device as low as possible. Ball slides 100, 102 are used due to the fact that actuators 50 and 52 have a stroke length of plus or minus 0.180 inches and yet there exists only plus or minus 0.015 inches of clearance between the coil and field portions of each actuator. Were one actuator to translate the proof mass frame 14 past plus or minus 0.015 inches, it would bind the other actuator. Mounting the actuators on the linear ball slide mechanisms allows free lateral translation, thereby preventing the binding problems due to any motion of the opposing actuator. When one actuator moves past plus or minus 0.015 inches, the other actuator simply translates along its ball slide mount thereby eliminating any binding problems. The linear ball slide mechanisms themselves become a part of the proof mass for the opposing degree of freedom when the actuators are moving. In other words, if actuator 52 pushes against proof mass frame 14, it will move the proof mass and actuator 50. Thus, the actuators themselves become a part of the proof mass for the opposing axis.

In addition, the actuators are mounted such that the moving half of the actuator, the permanent magnet section, becomes a part of the proof mass of the system. This design feature reduces any added mass to the system immensely. The Del-tron ball slide mechanisms 100 and 102 allow translations plus or minus 0.25 inches to take place, and were able to support four pounds of force. This capability coincides well with the actuators which were specified to be able to produce a maximum of three pounds of force. Additionally, the ball slide mechanisms weigh only approximately 0.30 ounces each. To further inhibit binding of the actuators, each is guided along it axis of force application by guide pin 132 fitted into aluminum adapter plate 130 placed between ball slide mechanism 100 and the field end of actuator 52. Teflon bushing 134 is press fit into proof mass structure frame 14 and then reamed to make sure that the bushing, after insertion, has the proper inner diameter for the application. Guide pin 132 is then press fit into the aluminum adapter plates and inserted into bushing 134. The end result of this arrangement is that proof mass frame 14 slides along guide pin 132 and the actuators themselves do not have to provide forces orthogonal to their axis of operation.

The resulting linear bearing exhibited excellent characteristics when finally assembled. Side to side play was minimal and the proof mass frame slid freely along the guide pins. Any friction is beneficial to the operation of the device in that the sliding ball mechanisms provide damping to the movement of proof mass frame 14 which leads to greater control system stability. To prevent binding, the Teflon to stainless steel interface between bushing 134 and guide pin 132 can be lubricated with machine oil to reduce friction between the two surfaces.

Proof mass frame 14 serves as the inertia against which actuators 50 and 52 exert force to stabilize the wearer's wrist. Proof mass frame 14 is made of aluminum and consists of tungsten weights 80 and 82, both the field and coil portions of actuators 50 and 52, adapter plates 130 and 131, the teflon inserts, the cores and extension rods of the LVDTs, and the sliding arm portion of the Del-tron ball slides. The shape of proof mass frame 14 was designed to encompass the wrist but may be modified by those skilled in the art to encompass other body parts or even tools or instruments. Tungsten weights 80 and 82 are added to boost the inertia of the proof mass. Weights 80 and 82 can then be easily changed, or removed entirely, depending on the specific design.

The center of mass of the system is, in one embodiment, within 0.125 inches from the intersecting axis of actuation of actuators 50 and 52. Epoxy adhesive is used to secure actuators 50 and 52 in housing 60 and 62, respectively, and the magnetized ends of the actuators, referred to as the field ends, are mounted to the proof mass frame due to the fact that they are the most massive. The electric ends of the actuators, referred to as the "coil" ends, are mounted to the linear ball slide mechanisms. To facilitate mounting the actuators to the ball slide mechanisms, small aluminum adapter plates 130, 131, FIG. 13 are secured to the linear bearings with screws and the actuator coil ends are secured to the adapter plate with screws.

The accelerometers are mounted on accelerometer mounts 200 and 202, FIG. 9 such that the input axis of each accelerometer is parallel with the force axis of the corresponding actuator 50, 52. Mounting the accelerometers in this position allows the elimination of any offset between the input of the accelerometer and the output axis of the actuators. Longitudinal centering of actuators 50, 52 is desired due to the fact that the actuators cannot be allowed to rest at one end or the other of their travel and then be expected to successfully move in an approximate sine wave shape. If the actuators were to rest against one of their stops, and then be required to move further in the same direction, stabilization would be ineffective. Centering the actuators allows them to start their motion from the middle of their full range of motion and successfully move in a sinusoidal fashion.

Figure 12:
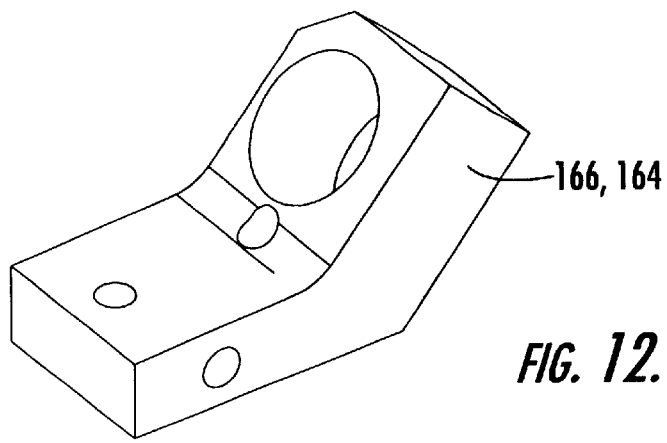
FIG. 12 is a three dimensional view of the LVDT mounting bracket component of the tremor suppressing wrist cuff shown in FIG. 9.

To that end, a position control loop for actuator position is effected by LVDTs 160 and 165 due to their relatively small size, completely electrical operation, and low mass. Lucas-Schaevitz Model 250-MHR LVDTs are preferred because they provide a precise measurement of a plus or minus 0.25 inch range. LVDT sensors 160, 165 are mounted by attaching the core of each LVDT to the wrist/actuator mount while the moveable part of the LVDT is mounted to the aluminum adapter plate of the opposing axis. The LVDT mounts 166, 164, FIG. 12 are machined from ABS Plastic and Helli-Coil inserts are added to the mounts so that they can be screwed to the wrist mount. A thin extension rod is threaded into the aluminum adapter plates located between the ball slide mechanisms and the actuators, and the LVDT core so that the core is in the proper location for a position sensing. In this way, the LVDTs are able to measure the distance between the wrist mount and the aluminum adapter plates, which is an indication of the motion of the actuators.

The resulting system had a mass of approximately 0.539 kilograms resulting in a very lightweight and compact design. Shielding may be required due to the use of the servo amplifier used to drive the voice coil actuators because it is a pulse width modulated unit that utilized a 33 kilohertz switching frequency. Since the LVDTs use relatively low level 10 kilohertz excitation and return signals, the shielding eliminates erroneous readings from the actuators.

In FIG. 9, actuators 50 and 52 are centered with respect to mount 12. Ball slides 100 and 102 and guide pins 132, 133 are also centered.

In FIG. 10, actuators 50 and 52 are in their fully extended positions. As such, proof mass frame 14 is shown in a position moved away from wrist mount 12 along both possible axes of motion. In FIG. 10, sliding arm 138 of ball slide mechanism 100 has translated to allow actuator 50 to push proof mass frame 14 away from wrist mount 12. FIG. 10 also shows how proof mass frame 14 has moved up on guide pins 132 and 133.

In FIG. 11, proof mass frame 14 has moved away from wrist mount 12 due to the extension of actuator 50 and the contraction of actuator 52. Proof mass frame 14, however, has moved toward wrist mount 12 by the contraction of actuator 52. Therefore, the position of actuator 50 is extended while the position of actuator 52 is contracted. Ball slide mechanism 102 has shifted to the right in FIG. 11 in response to the downward movement of actuator 52.

Figure 15:
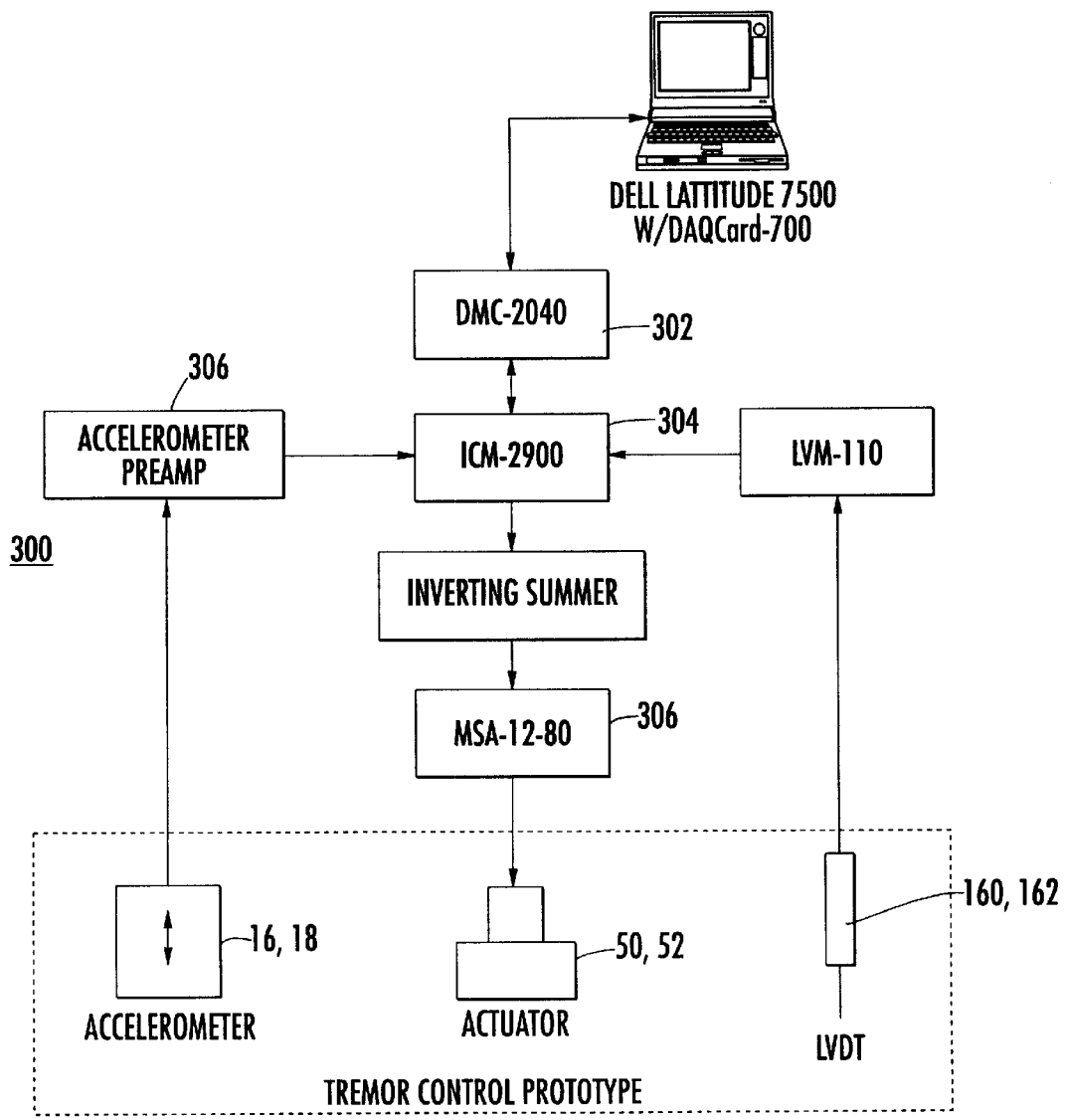
FIG. 15 is a block diagram showing the primary components associated with the controller for the active tremor control system of this invention.

Controller system 300, FIG. 15 of this invention operates as a linear time invariant control system employing four independent control loops, two loops for each of the two actuator axes. One of the loops maintains the position of the proof mass frame around an approximately centered location mitigating the gravitational force and the other control loop serves to move the proof mass frame in response to accelerations of the wrist in order to quell tremors. By tuning the bandwidths of each of the loops so that they do not overlap, there is no conflict between them. Controller 300 includes a digital motion controller and certain associated accessories available from Galil Motion Controls, Inc. of Rocklin, Calif. such as a Model DMC-2040 Universal Serial Bus 302 stand alone controller and a Model ICM-2900 interconnect module 304 and a model MSA-12-80 brush-type servo amplifier 306 as well as a CPS-12-24 power supply (not shown). The DMC-2040 includes a 32-bit microprocessor, digital signal processing chips and an analog-to-digital and digital-to-analog converters. The DMC-2040 is connected via a 100 pin cable to the ICM-2900 interconnect module 304. The DMC-2040 is a four-axis unit thus allowing control of four individual axis of motion. This configuration is ideal due to the fact that the tremor controller includes four control loops, two axis each, having a position and acceleration control loop. In an analog feedback mode, the DMC-2040 accepts a plus or minus ten volt signal from the LVDTs 160, 162 and accelerometers 16, 18 and the control loop user defined analog feedback values as their desired value. For example, for an LVDT reading plus or minus 10 volts full-scale, the user can instruct the DMC-2040 to maintain the LVDT output at zero volts which results in a centered arrangement. The DMC-2040 is then able to provide feedback at approximately 1 kilohertz bandwidth.

The pin assignments on the 25-pin tremor controller connector are as follows:

| Connector Pin # | Connection To |
| --- | --- |
| 1 | Positive x actuator terminal |
| 2 | Positive y actuator terminal |
| 3 | Not connected |
| 4 | Brown x LVDT wire |
| 5 | Yellow x LVDT wire |
| 6 | Black y LVDT wire |
| 7 | Brown y LVDT wire |
| 8 | Yellow y LVDT wire |
| 9 | Not connected |
| 10 | x accelerometer ground |
| 11 | x accelerometer power |
| 12 | y accelerometer signal |
| 13 | Not connected |
| 14 | Negative x actuator terminal |
| 15 | Negative y actuator terminal |
| 16 | Not connected |
| 17 | Green/Blue x LVDT wires |
| 18 | Red x LVDT wire |
| 19 | Black y LVDT wire |
| 20 | Green/Blue y LVDT wires |
| 21 | Red y LVDT wires |
| 22 | Not connected |
| 23 | x accelerometer signal |
| 24 | y accelerometer +5 Volts power |
| 25 | y accelerometer ground |

The connections to the ICM-2900 interconnect module are as shown in the following table:

| Signal | Connection To | ICM-2900 Terminal Label |
|---|---|---|
| x axis accelerometer | x axis analog input | ANALOG1 |
| y axis accelerometer | y axis analog input | ANALOG2 |
| x axis LVDT | z axis analog input | ANALOG3 |
| y axis LVDT | w axis analog input | ANALOG4 |
| signal grounds | analog input grounds | ANAGND |
| x accel motor command | x axis motor command | MOCMDX |
| y accel motor command | y axis motor command | MOCMDY |
| x LVDT motor command | z axis motor command | MOCMDZ |
| y LVDT motor command | w axis motor command | MOCMDW |
| x accel amplifier enable | x axis amplifier enable | AMPENY |
| y accel amplifier enable | y axis amplifier enable | AMPENY |
| x LVDT amplifier enable | z axis amplifier enable | AMPENZ |
| y LVDT amplifier enable | w axis amplifier enable | AMPENW |

Further details concerning the design of the system described herein are disclosed in the thesis entitled "Active Tremor Control of Human Motion Disorder" by Gary Ellis Hall, Jun. 2001, incorporated herein by this reference and available at http://web.mit.edu/ghall/www.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the following claims:

What is claimed is:

1. A lightweight, wearable, and balanced active tremor control system comprising:
   a mount;
   a proof mass frame moveable with respect to the mount;
   at least one actuator on the proof mass frame for imparting a force on the mount;
   a motion sensor for detecting motion of the mount; and
   a controller for driving the actuator in response to the motion sensor.

2. The tremor control system of claim 1 in which there are two actuators orthogonally oriented on the proof mass frame.

3. The tremor control system of claim 2 in which the actuators are voice coil linear actuators.

4. The tremor control system of claim 1 in which there are two motion sensors orthogonally oriented on the mount.

5. The tremor control system of claim 4 in which the motion sensors are accelerometers.

6. The tremor control system of claim 1 in which the proof mass frame includes a central section attached to the mount and a pair of arms depending therefrom.

7. The tremor control system of claim 6 further including a weight attached to the end of each arm.

8. The tremor control system of claim 6 in which the central section includes two angled actuator housings.

9. The tremor control system of claim 6 in which the mount is unitary and spans the central section of the proof mass frame.

10. The tremor control system of claim 1 in which the mount includes two planar side surfaces and a top planar surface.

11. The tremor control system of claim 1 in which there is a ball slide mechanism interconnecting the proof mass frame and the mount.

12. The tremor control system of claim 11 in which a housing portion of the ball slide mechanism is fixed with respect to the mount.

13. The tremor control system of claim 12 in which a sliding arm portion of the ball slide mechanism is physically connected to the actuator.

14. The tremor control system of claim 1 in which the actuator has a force axis, the motion sensor is an accelerometer with an input axis, and the accelerometer is mounted with respect to the mount such that the input axis is parallel to the force axis.

15. The tremor control system of claim 1 further including means for fixing the position of the proof mass with respect to the mount.

16. The tremor control system of claim 15 in which said means further senses the position of the proof mass frame with respect to the mount.

17. The tremor control system of claim 16 in which said means includes a linear voltage displacement transducer, one portion of which is attached to the mount, the other portion of which is attached to the proof mass frame.

18. A tremor suppression wrist cuff comprising:
   a wrist mount including a top surface and angled surfaces adapted to be disposed over the ulna and radius bones of the human wrist, respectively,
   a proof mass frame moveable with respect to the wrist mount; and
   a pair of actuators each connected to the proof mass frame and an angled surface of the wrist mount to apply force to the angled surfaces of the wrist mount and to the ulna and radius bones of the wrist.

19. The wrist cuff of claim 18 in which the proof mass frame includes angled actuator housings and each actuator has a magnet disposed in an actuator housing.

20. The wrist cuff of claim 18 further including a pair of ball slide mechanisms each including an arm slidable in a housing to allow the actuators to move laterally.

21. The wrist cuff of claim 20 in which each actuator has a coil mounted to an arm and wherein the housing of each ball slide mechanism is mounted to an angled surface of the wrist mount.

22. The wrist cuff of claim 21 further including a pair of guide pins slidably disposed through the proof mass frame and each connected on one end to an adapter plate which secures the coil of each actuator to its respective arm of the ball slide mechanism to guide the actuators.

23. The wrist cuff of claim 21 further including a pair of transformers each including a core mounted to the top surface of the wrist mount and a moveable part mounted to an adapter plate for sensing and adjusting the position of the proof mass frame relative to the wrist mount.

24. The wrist cuff of claim 18 in which the proof mass frame includes a pair of arms depending therefrom.

25. The wrist cuff of claim 24 in which there is a weight attached to each arm so that the center of mass of the wrist cuff is at the center of the wrist when worn by a user.

26. An active tremor control system comprising:
   a mount attachable to a device or a body part;
   a proof mass frame moveably joined with respect to the mount;
   at least one sensor for detecting vibrations of the mount; and
   at least one actuator disposed to apply a force to the proof mass frame with respect to the mount to thereby suppress vibrations of the mount.

27. The active vibration control system of claim 26 in which there are two independently driven actuators for adjusting the position of the proof mass frame with respect to the mount.

* * * * *